United States Patent
Wehrmann et al.

(10) Patent No.: US 6,696,543 B2
(45) Date of Patent: Feb. 24, 2004

(54) POLYESTER POLYCARBONATES OF PARTICULAR DIPHENOLS

(75) Inventors: Rolf Wehrmann, Krefeld (DE); Helmut-Werner Heuer, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/224,004

(22) Filed: Aug. 20, 2002

(65) Prior Publication Data

US 2003/0120024 A1 Jun. 26, 2003

(30) Foreign Application Priority Data

Aug. 24, 2001 (DE) .......................... 101 41 621

(51) Int. Cl.[7] .............................................. C08G 64/00
(52) U.S. Cl. ................... 528/196; 264/176.1; 264/219; 369/47; 369/59.11; 528/198
(58) Field of Search ............................... 528/196, 198; 369/47, 59.11; 264/176.1, 219

(56) References Cited

U.S. PATENT DOCUMENTS

| | | | |
|---|---|---|---|
| 3,859,097 A | 1/1975 | Hamb et al. | 96/87 R |
| 4,983,706 A | 1/1991 | Fontana et al. | 528/176 |
| 5,025,081 A | 6/1991 | Fontana et al. | 528/176 |
| 5,134,220 A | 7/1992 | Serini et al. | 528/190 |
| 5,274,068 A | 12/1993 | Boden et al. | 528/179 |
| 5,408,027 A | 4/1995 | Haese et al. | 528/196 |

FOREIGN PATENT DOCUMENTS

| | | |
|---|---|---|
| EP | 443 058 | 8/1991 |
| JP | 3-162413 | 7/1991 |
| JP | 8-123050 | 5/1996 |
| JP | 10-251395 | 9/1996 |

OTHER PUBLICATIONS

Patent Abstracts of Japan vol. 1998, No. 14, Dec. 31, 1998 & JP 10 251395 A. (Mitsubishi Gas Chem Co. Inc.) Sep. 22, 1998 in der Anmeldung erwahnt.

P. Livent, Weizheng Xu: "Reaction of Resorcinol with alpha, beta–Unsaturated Ketones".

J. Org. Chem., Bd. 63, Nr. 3, Jan. 22, 1998, Seiten 636–641, XP002219520, Seite 646, Spalte 1; Tabelle 1 Seite 639, Speite 1 Formel 4 und 17.

Database CA Onlinel Chemical Abstracts Service, Columbus, Ohio, US; Yoshida, Akira et al:. "Electrophotographic photoreceptor containing polyarylate, process cartridge, and apparatus" retrieved from STN Database accession No. 133:185491 XP002219575 Zusammenfassung & JP 2000 227666 A (Canon Inc., Japan) Aug. 15, 2000.

Primary Examiner—Terressa Boykin
(74) Attorney, Agent, or Firm—Joseph C. Gil; Aron Preis

(57) ABSTRACT

Polyestercarbonate resin is disclosed having a molecular structure that contains units derived from dicarboxylic acids and units derived from at least one diphenol selected from the group consisting of formula (IIa) and (IIb)

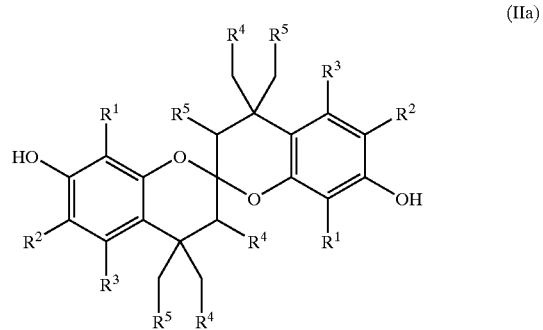

(IIa)

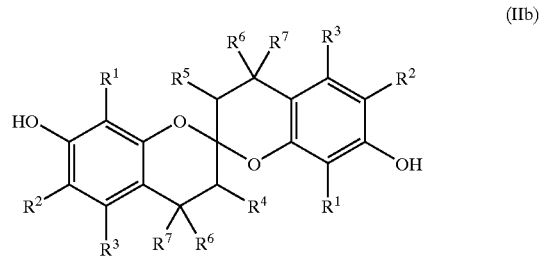

(IIb)

in which $R_1$ to $R_7$ each independently of the others represents hydrogen, halogen, a $C_1$- to $C_{12}$-alkyl radical, a $C_6$- to $C_{19}$-aryl radical, a $C_7$- to $C_{12}$-aralkyl radical. Also disclosed are the processes for their preparation, and their use in the production of molded articles and extrudates.

11 Claims, No Drawings

POLYESTER POLYCARBONATES OF PARTICULAR DIPHENOLS

FIELD OF THE INVENTION

The present invention relates to thermoplastic molding compositions and in particular to compositions that contain polyester polycarbonates.

SUMMARY OF THE INVENTION

Polyestercarbonate resin is disclosed having a molecular structure that contains units derived from dicarboxylic acids and units derived from at least one diphenol selected from the group consisting of formula (IIa) and (IIb)

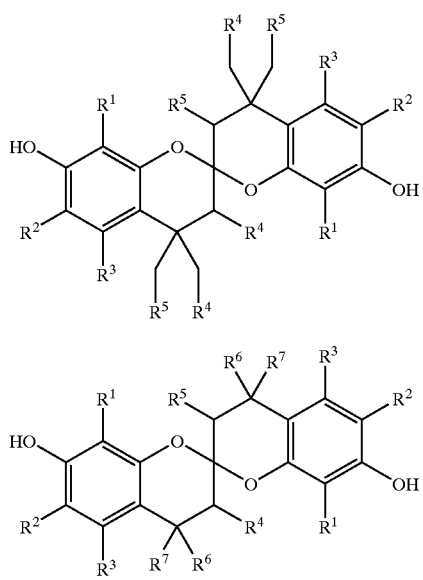

in which $R_1$ to $R_7$ each independently of the others represents hydrogen, halogen, a $C_1$- to $C_{12}$-alkyl radical, a $C_6$- to $C_{19}$-aryl radical, a $C_7$- to $C_{12}$-aralkyl radical. Also disclosed are the processes for their preparation, and their use in the production of molded articles and extrudates.

BACKGROUND OF THE INVENTION

In the course of new developments of optical data carriers, the requirements made of the carrier material are becoming increasingly more demanding and require the targeted development of new materials, for example, with the aim of achieving lower birefringence and lower water absorption, especially for the shorter writing and reading wavelengths which are to be expected in the future and which represent new challenges.

Low birefringence and low water absorption are not the only important properties for the substrate materials of optical data carriers; however, a combination of further properties that is as optimum as possible is required, such as high transparency, dimensional stability under heat, flowability, strength, high purity, low density, low contents of inhomogeneities or particulates and, especially, low costs of raw material and production.

Currently proposed materials for such applications fail to meet one or more of those requirements, and there is therefore a need for new materials for higher storage densities.

Polyester polycarbonates of linear or cyclic difunctional aliphatic carboxylic acids, diphenols and carbonate precursors are described, for example, in EP-A 433 716, U.S. Pat. No. 4,983,706 and U.S. Pat. No. 5,274,068, which describe various processes for their synthesis. It is known to the person skilled in the art that the incorporation of dicarboxylic acids leads to a lowering of the glass transition temperature and to an increase in flowability. For use as substrate materials, however, the lowered glass transition temperature means a limitation on the usability of the disks, because their climate resistance is reduced thereby. In addition, owing to the polar ester groups, such products have high water absorption, which is disadvantageous for use in optical data storage media. As EP-A 433 716 teaches, the carboxylic acids known for polyester polycarbonates can be incorporated in a significant amount in the interfacial process only by means of a complex, multi-stage procedure.

Polyester polycarbonates of linear and longer-chain dicarboxylic acids, in particular, also exhibit an undesirable tendency to crystallize, which has a particularly adverse effect in the case of very slow cooling, which may be necessary for the forming of very fine structures and to avoid process-related birefringence.

Dimer fatty acids as possible acid components in polyester polycarbonates are listed, for example, in DE-A 43 06 961, U.S. Pat. No. 5,134,220 and EP-A 443 058. A more precise definition of the acids to be used is not given. However, thermooxidative problems occur with non-hydrogenated dimer fatty acids. In addition, the customary commercial products contain more than 3 mol % of carboxylic acids having a basicity of three or more, which leads to a high viscosity at zero rate of shear, which is undesirable in the forming of microstructures such as pits or grooves. For that reason, such polyester polycarbonates have generally been regarded hitherto as unsuitable for substrates for optical data storage media.

Particular copolycarbonates based on spirobischromans and other diphenols are described in JP-A 10251395 and JP-A 08123050 as binders for photoreceptors. Spirobischroman-based polymers, for example polyethers or polycarbonates, are disclosed in JP-A 3162413, the latter spirochroman types are composed solely of hydroquinone and acetone, that is to say they have a strict 1,4 linkage.

The products described in the literature are polymers that have too high a glass transition temperature for use as the substrate material for optical data storage media.

Accordingly, the object underlying the invention is to provide polyester polycarbonates that do not have the disadvantages mentioned above but, in particular, have improved optical properties and may readily be prepared.

DETAILED DESCRIPTION OF THE INVENTION

Surprisingly, that object is achieved by polyester carbonates which are prepared by one of the conventional preparation processes for polycarbonates, characterized in that there are used in the preparation, in addition to the conventional carbonic acid derivatives, also dicarboxylic acids of formula (I)

$$HOOC-T-COOH \qquad (I)$$

wherein T represents a branched or linear, saturated or unsaturated alkyl, arylalkyl or cycloalkyl moiety of from 8 to 40 carbons, preferably saturated linear alkyldicarboxylic acids having from 8 to 40 carbons, particularly preferably having from 12 to 36 carbons,
and, optionally proportionately in addition to the conventional diphenols, particular diphenols of formula (IIa) and/or (IIb)

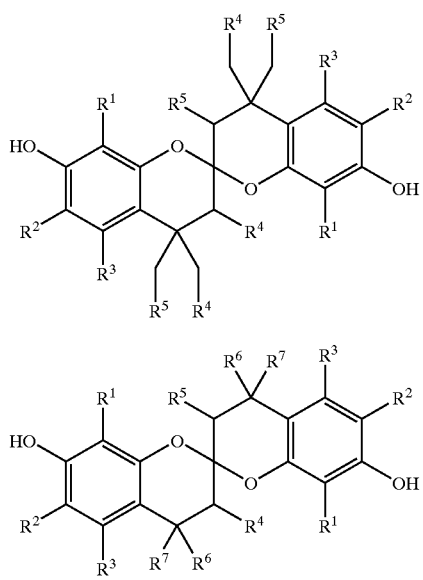

in which
$R_1$ to $R_7$ each independently of the others represents hydrogen, halogen, a $C_1$- to $C_{12}$-alkyl radical, preferably a $C_1$- to $C_3$-alkyl radical, particularly preferably methyl, a $C_6$- to $C_{19}$-aryl radical, preferably a phenyl radical, a $C_7$- to $C_{12}$-aralkyl radical, preferably phenyl-$C_1$- to $C_4$-alkyl, particularly preferably hydrogen, halogen, preferably chlorine or bromine.

"Proportionately" in this context means that the particular diphenols of formulae IIa and IIb represent a proportion >0% of the total amount of diphenols used.

If no further conventional diphenols are used, the proportion of diphenols of formulae IIa and IIb is 100% of the diphenols used. In all other cases, the sum of the molar amounts of each of the individual diphenols is 100%. In such mixtures of diphenols, the proportion of diphenols of formulae IIa and IIb is preferably >10 mol %, particularly preferably >20 mol % and most particularly preferably >25 mol %. All conventional diphenols are suitable as diphenols used additionally in combination with the diphenols of formulae IIa and IIb.

Suitable dicarboxylic acids according to the invention are fatty acids, particularly preferably hydrogenated dimer fatty acids.

Examples of dicarboxylic acids of formula (I), or mixtures of such fatty acids, are
sebacic acid,
dodecanedioic acid,
hydrogenated dimer fatty acids, such as, for example, Pripol 1009 from Uniqema.

Pripol 1009 from Uniqema is a mixture of hydrogenated dimer fatty acids which, according to Uniqema, has approximately the following composition:

-continued

| Structure (different isomers in each case) | Data Uniqema |
|---|---|

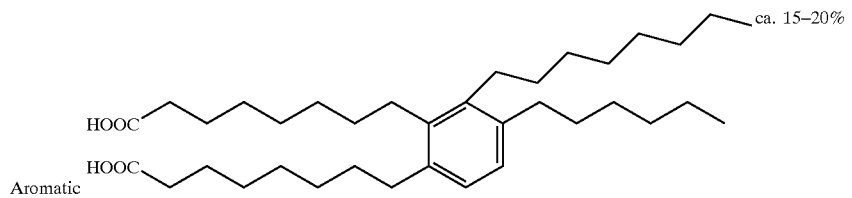

Aromatic ca. 15–20%

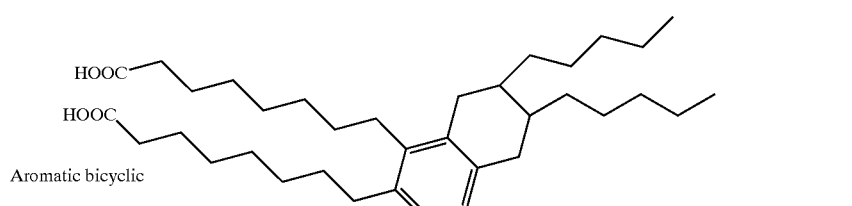

Aromatic bicyclic

Dodecanedioic acid and Pripol 1009 are particularly preferred.

A small amount of mono- and poly-functionalized fatty acids may also be present. Products having very small contents of such components, especially having small contents of acids having a functionality of three or more, are especially suitable for the preparation of the polyester polycarbonates according to the invention. Preference is given, therefore, to dimer fatty acids having a content of less than approximately 1.5%, determined by gas chromatography, of acids having a functionality of three or more. The invention also includes mixtures of dimer fatty acids with other difunctional carboxylic acids having from 4 to 40 carbon atoms, such as adipic acid, sebacic acid, α,ω-dodecanedicarboxylic acid, terephthalic acid, cis- or trans-9-octadecene-α,ω-dicarboxylic acid, or hydroxycarboxylic acids having from 4 to 40 carbon atoms, such as salicylic acid or p-hydroxybenzoic acid.

Within the scope of the invention, the dimer fatty alcohols obtained from dimer fatty acids by reduction, or mixtures of esters of dimer fatty alcohols with dimer fatty acids, may also be used and reacted to prepare the inventive polyester polycarbonates.

Particularly preferred diphenols of formulae (IIa) and (IIb) are:

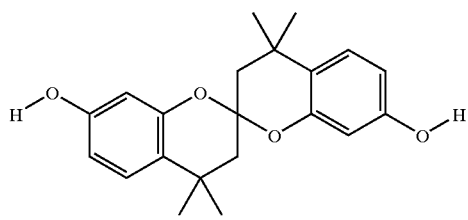

-continued

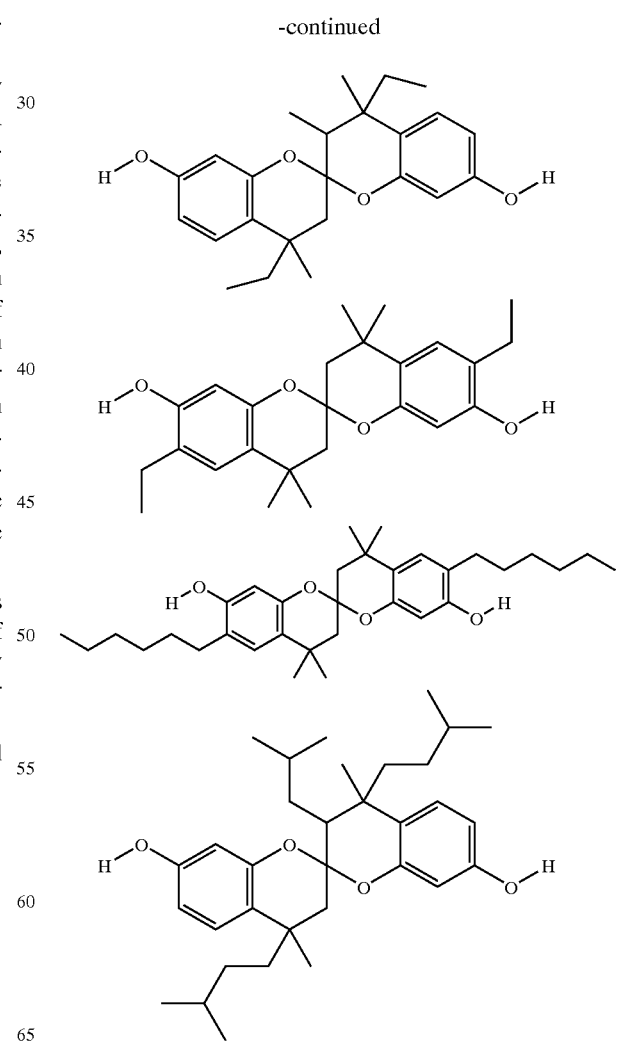

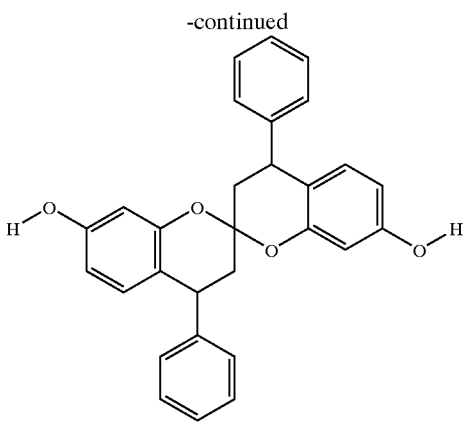

Most particularly preferred is the diphenol (III), which is obtained from resorcinol and acetone.

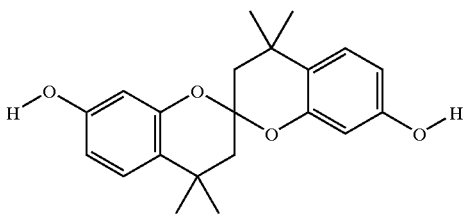
(III)

The compounds of formulae IIa, IIb and III may be used either individually or in mixtures with one another.

With the exception of the compounds in which $R^1$ to $R^5$ in formula IIa are hydrogen and $R^6$ and $R^7$ in formula IIb are simultaneously methyl groups, the diphenols of formulae IIa, IIb and III are novel, and the present Application relates thereto and to their preparation and their use in the preparation of polyester carbonates.

The polyester polycarbonates according to the invention may be illustrated, by way of example and preference, but in a non-limiting manner, by the following structural description of the polyester carbonates:

Polyester carbonates containing repeating bifunctional structural units A according to formula (IV)

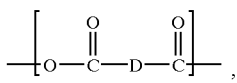
(IV)

wherein the square brackets characterize an optionally repeating structural unit, D represents a mixture of divalent hydrocarbon radicals which contain 30 to 42 carbon atoms, preferably 32 to 38 carbon atoms, particularly preferably 34 carbon atoms. D corresponds substantially to formula IVa and/or IVb and/or IVc and/or IVd and/or IVe.

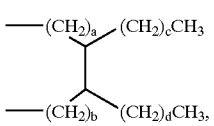
(IVa)

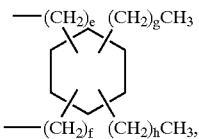
(IVb)

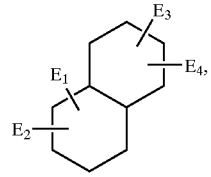
(IVc)

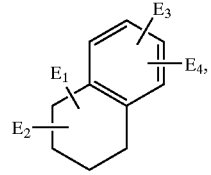
(IVd)

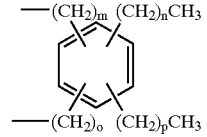
(IVe)

wherein $E_1$, $E_2$, $E_3$ and $E_4$ in formulae Ic and Id each represents one of the substituents —$(CH_2)_i$—, —$(CH_2)_j$—, —$(CH_2)_kCH_3$ and —$(CH_2)_lCH_3$ and a, b, c, d, e, f, g, h, i, j, k, l, m, n, o and p each independently of the others represents an integer of 1 to 10, and at least one of the further bifunctional structural units B, which are different from A, according to formula (V)

$$-\!\!+\!\!O\!-\!R\!-\!O\!-\!\underset{\underset{O}{\|}}{C}\!\!+\!\!-,$$ (V)

wherein the square brackets here characterize an optionally repeating structural unit, and formulae A and B may optionally overlap in the region of the carbonyl group, wherein the radical —O—R—O— represents diphenolate radicals derived from the above-mentioned phenols of formulae (IIa) and (IIb) or from conventional diphenols, such as bisphenol A or bisphenol TMC.

In the present context, "conventional diphenols" means the diphenols that may conventionally be used for the preparation of polycarbonates, see, for example, U.S. Pat. Nos. 3,028,635, 2,999,835, 3,148,172, 2,991,273, 3,271, 367, 4,982,014 and 2,999,846, DE-A 1 570 703, 2 063 050, 2 036 052, 2 211 956 and 3 832 396, French Patent Specification 1 561 518, the monograph "H. Schnell, Chemistry and Physics of Polycarbonates, Interscience Publishers, New York 1964", p. 77 ff, and JP-A 62039/1986, 62040/1986 and 105550/1986, all incorporated herein by reference.

Illustrative conventional diphenols include 2,2-bis(4-hydroxyphenyl)-propane (bisphenol A), 1,1-bis(4-hydroxyphenyl)-3,3,5-trimethylcyclohexane (bisphenol TMC), 1,3-bis[2-(4-hydroxyphenyl)-2-propyl]benzene, 1,1-bis(4-hydroxyphenyl)-1-phenylethane, 1,1-bis(4-hydroxyphenyl)-cyclohexane (bisphenol Z), especially 2,2-bis(4-hydroxyphenyl)propane (bisphenol A) and 1,1-bis(4-hydroxyphenyl)-3,3,5-trimethylcyclohexane (bisphenol TMC), most particularly preferably 2,2-bis(4-hydroxyphenyl)propane (bisphenol A).

In addition, there may be used for the preparation of the polyester polycarbonates according to the invention also bifunctional monophenols, such as resorcinol, hydroquinone or their derivatives mono- or poly-substituted by $C_1$- to $C_{12}$-alkyl, $C_6$- to $C_{19}$-aryl or $C_7$- to $C_{19}$-aralkyl.

It has been found that substrates of the polyester polycarbonates according to the invention are distinguished by surprisingly particularly low water absorption, astonishingly low birefringence, very low tendency to crystallize, low refractive index, good flowability and low density, as well as low glass transition temperature.

The substrates for data carriers of the novel polyester polycarbonates also possess high transparency, good mechanical properties, especially at low temperatures, and high flowability.

Within the context of this invention, hydrogenated dimer fatty acids are to be understood as being acids that may be obtained by dimerisation of unsaturated monobasic fatty acids having from 16 to 22 carbon atoms and subsequent hydrogenation. The required acids may be obtained, for example, from vegetable or animal sources. Synthesis and properties are described, for example, in Encyclopedia of Chemical Technology, Vol. 8, 4th ed., John Wiley & Sons: 1993, page 223–237.

Such hydrogenated dimer fatty acids may still contain small amounts of unsaturated aliphatic groups. Dimer fatty acids having an iodine number of less than approximately 15 are preferred.

The diphenols of formulae (IIa) and (IIb) may be prepared according to the reaction sequences shown in Schemes 1 and 2.

Scheme 1:

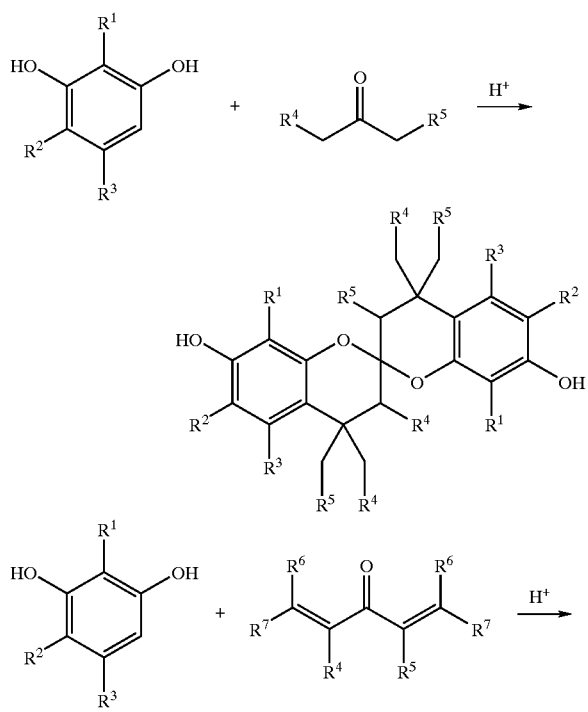

-continued

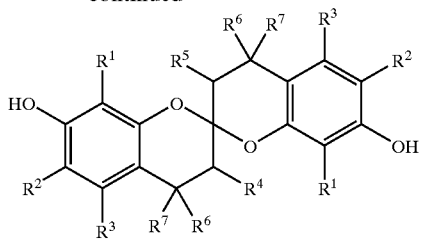

The diphenols prepared according to Scheme 1 are obtained after condensation of ketones (e.g. acetone, methyl ethyl ketone, etc., Aldrich) and optionally substituted resorcinol derivatives (e.g. 4-hexylresorcinol, Aldrich) with removal of water under acid conditions. Alternatively, phorone (2,6-dimethyl-2,5-heptadien-4-one) (Aldrich) or substituted phorones may also be used as starting materials for the condensation. Suitable acids are inorganic acids, such as, for example, sulfuric acid. Acid cation exchangers, such as, for example, Lewatite®, are also possible. Corresponding condensation methods for the preparation of spiro components by reaction of resorcinol with ketones are described in JP-A 10265476. The condensations are conventionally carried out in customary solvents, such as, for example, hydrocarbons, toluene, NMP or chlorobenzene, at temperatures of from 20 to 200° C., preferably from 30 to 180° C., particularly preferably from 50 to 150° C. and most particularly preferably from 60 to 130° C.

Preferred polyester polycarbonates according to the invention are those which contain from 0.5 to 49 mol %, preferably from 2 to 40 mol %, particularly preferably from 5 to 20 mol %, based on 100 mol % of the bifunctional structural units A and B, of structural units A.

Compounds and embodiments that fall within the definitions mentioned as being preferred, particularly preferred or most particularly preferred, or that use the definitions or explanations and parameters mentioned within the scope of preferences, are preferred, particularly preferred or most particularly preferred.

The definitions or explanations and parameters mentioned above in general or within the scope of preferences can, however, also be combined with one another as desired, that is to say between the respective ranges and preferences.

The polyester polycarbonates according to the invention are distinguished in particular by a glass transition temperature of from 120 to 195° C., preferably from 125 to 180° C., particularly preferably from 130 to 170° C. and most particularly preferably from 135 to 165° C.

The polyester polycarbonates according to the invention are further distinguished by a low water absorption of <0.40%, preferably <0.38%, particularly preferably <0.36%, most particularly preferably <0.35% at saturation.

"Saturation" in this context is to be understood as being the value achieved after 14 days' humid storage at 94% relative humidity and 30° C. The water content is then determined by means of quantitative Karl-Fischer titration.

The substrates according to the invention may be prepared by the three known methods (see H. Schnell, "Chemistry and Physics of Polycarbonates", Polymer Review, Volume IX, page 27 ff; Interscience Publishers, New York 1964, and DE 1495 626 A, DE 22 32 877 A, DE 27 03 376 A, EP 274 544 A, DE 30 00 610 A, DE 38 32 396 A) incorporated herein by reference.

1. By the Solution Process in Disperse Phase, the So-Called "Two-Phase Interfacial Process"

In this process, the diphenols and bifunctional acids to be used are dissolved in an aqueous alkaline phase. To that end, the chain terminators required for the preparation of the polyester polycarbonates according to the invention are optionally dissolved in amounts of from 1.0 to 20 mol %, based on mols of diphenols plus acid to be used according to the invention, in an aqueous alkaline phase, preferably sodium hydroxide solution, or are added thereto and to an inert organic phase, without a solvent. The thus obtained material system is then reacted with phosgene in the presence of an inert organic phase which is preferably a solvent for polycarbonate. The reaction temperature is from 0° C. to 50° C.

The addition of the necessary chain terminators, branching agents and acids according to the invention my also take place during the phosgenation or as long as chlorocarbonic acid esters are present in the synthesis mixture, without a solvent, in the form of a melt, in the form of a solution in alkali or inert organic solvents.

The reaction may be accelerated by means of catalysts, such as tertiary amines or onium salts. Preference is given to tributylamine, triethylamine and N-ethylpiperidine, as well as to tetrabutylammonium, tetraethylammonium and N-ethylpiperidinium salts.

In addition to or instead of the diphenols, their chlorocarbonic acid esters and/or bischlorocarbonic acid esters may also be used or metered in during the synthesis. Instead of the dimer fatty acids, it is also possible to use their acid chlorides. Suitable solvents are, for example, methylene chloride, chlorobenzene, toluene and mixtures thereof.

2. By the Solution Process in Homogeneous Phase, also Called the "Pyridine Process"

In this process, the diphenols and acids according to the invention are dissolved in organic bases such as pyridine, optionally with the addition of further organic solvents, and then, as described under 1., the chain terminators and branching agents required for the preparation of the polyester polycarbonates according to the invention are optionally added.

The whole is then reacted with phosgene. The reaction temperature is from 10 to 50° C. Suitable organic bases, other than pyridine, are, for example, triethylamine, tributylamine, N-ethylpiperidine, as well as N,N-dialkyl-substituted anilines, such as N,N-dimethylaniline. Suitable solvents are, for example, methylene chloride, chlorobenzene, toluene, tetrahydrofuran, 1,3-dioxolane and mixtures thereof.

In addition to the diphenols, up to 50 mol %, based on the phenols used, of their bischlorocarbonic acid esters may also be used. Some or all of the fatty acids according to the invention may be replaced by their acid chlorides. The addition of the necessary chain terminators, branching agents and acids according to the invention may also take place during the phosgenation or as long as chlorocarbonic acid esters are present in the synthesis mixture, without a solvent, in the form of a melt or in the form of a solution in inert organic solvents.

Isolation of the polyester polycarbonates in processes 1 and 2 takes place in a known manner. Suitable processes for working up are especially precipitation, spray-drying, and evaporation of the solvent in vacuo.

3. By the Melt Transesterification Process

In the melt transesterification process, condensation is carried out, with the addition of diphenyl carbonate in stoichiometric amounts or in an excess of up to 40%, to diphenol melt/fatty acids, with the continuous removal by distillation of phenol and optionally of excess diphenyl carbonate, until a suitable molecular weight is reached or the reaction comes to a standstill. This is usually carried out under inert conditions, at approximately 280° C. and under an oil-pump vacuum. This process is carried out using conventional catalysts, such as alkali metal ions, for example Li, Na, K, transition metal compounds, for example those based on Sn, Zn, Ti or nitrogen or phosphorus bases, preferably ammonium and phosphonium salts, as a single-stage or two-stage process, that is to say with the optional separate condensation of the oligomers and of the polymer.

Phosphonium salts within the context of the invention are those of formula (V)

wherein $R^{1-4}$ may be the same or different $C_1$–$C_{10}$-alkyl radicals, $C_6$–$C_{10}$-aryl radicals, $C_7$–$C_{10}$-aralkyl radicals or $C_5$–$C_6$-cycloalkyl radicals, preferably methyl or $C_6$–$C_{14}$-aryl radicals, particularly preferably methyl or phenyl, and $X^-$ may be an anion, such as hydroxide, sulfate, hydrogen sulfate, hydrogen carbonate, carbonate, a halide, preferably chloride, or an alcoholate of the formula OR, wherein R may be $C_6$–$C_{14}$-aryl or $C_7$–$C_{12}$-aralkyl, preferably phenyl. Preferred catalysts are
tetraphenylphosphonium chloride,
tetraphenylphosphonium hydroxide,
tetraphenylphosphonium phenolate,
particularly preferably tetraphenylphosphonium phenolate.

Instead of the acids to be used according to the invention, it is possible to employ their aromatic or aliphatic esters, for example, methyl, ethyl, isopropyl or phenyl esters.

In a known manner, chain terminators and/or branching agents may be used concomitantly for the preparation of the polyester polycarbonates according to the invention. The corresponding chain terminators and/or branching agents are known inter alia from EP-A 335 214 (pages 3–5) and DE-A 30 07 934 (pages 8–9), and EP-A 411 433 (pages 4 and 5) and EP-A 691 361 (page 5). In addition, some or all of the branching agents and/or chain terminators may be replaced by dimer fatty acids having a higher content of tri- and/or mono-functional carboxylic acids.

It is also possible for the substrates of the polyester polycarbonates according to the invention to be mixed with different thermoplastic polymers in a weight ratio of from 2:98 to 98:2 and to be used in the form of blends.

The polyester polycarbonates according to the invention have molecular weights $M_W$ (weight average, determined by gel chromatography (Merck column combination consisting of PS4000, PS400 and PS40) after previous calibration on bisphenol A PC (calibration based on absolute values determined by means of light scattering and MALDI) of at least 6000, preferably from 7000 to 45,000, particularly preferably from 7000 to 40,000, most particularly preferably from 9000 to 40,000, especially from 9000 to 30,000.

It is possible to add to the polyester polycarbonates for the production of the data carriers according to the invention, before, during or after their processing, the additives conventional for thermoplastic polycarbonates, such as stabilizers, for example heat stabilizers, organic phosphites, optionally in combination with monomeric or oligomeric epoxides; UV stabilizers, especially those based on nitrogen-containing heterocycles, such as triazoles; optical brightening agents, flameproofing agents, especially fluorine-containing, such as perfluorinated salts of organic acids, polyperfluoroethylene, salts of organic sulfonic acids and combinations thereof; mold release agents; flow auxiliaries; flame retardants; colorants; pigments; antistatics; fillers and reinforcing agents, comminuted minerals, fibrous materials, for example, alkyl and aryl phosphites, phosphates, phosphanes, low molecular weight carboxylic acid esters, halogen compounds, salts, chalk, quartz, inorganic or organic nanoparticles, glass and carbon fibers, in the conventional amounts. Examples of such additives will be found described, for example, in WO 99/55772, p. 15–25, and in "Plastics Additives", R. Gächter and H. Müller, Hanser Publishers 1983.

The data carriers or other molded bodies according to the invention may be produced in a known manner by injection molding or injection stamping on known machines.

In addition to the described polyester polycarbonates, the invention relates also to extrudates and molded articles containing them, such as optical lenses, disks and films which contain the polyester polycarbonates according to the invention, and to the use of those polyester polycarbonates in the production of such molded bodies and extrudates. The excellent properties of the polyester polycarbonates are shown to advantage especially in the case of optical lenses and data storage media.

The following are mentioned as examples of possible applications of the polyester carbonate according to the invention, this list not being limiting:
1. Safety glazing, which, as is known, is required in many areas of buildings, motor vehicles and aircraft, as well as the visors of helmets.
2. Production of films, especially ski films.
3. Production of blow-molded articles (see, for example, U.S. Pat. No. 2,964,794), for example 1 to 5 gallon water bottles.
4. Production of transparent sheets, especially of hollow-chamber sheets, for example, for covering buildings such as railway stations, greenhouses and lighting installations.
5. Production of optical data storage media.
6. For the production of traffic light housings or road signs.
7. For the production of foamed materials (see, for example, DE-AS 1 031 507).
8. For the production of threads and wires (see, for example, DE-AS 1 137 167 and DE-OS 1 785 137).
9. As translucent plastics having a content of glass fibers for lighting purposes (see, for example, DE-OS 1 554 020).
10. As translucent plastics having a content of barium sulfate, titanium dioxide and or zirconium oxide or organic polymeric acrylate rubbers (EP-A 634 445, EP-A 269324) for the production of transparent and light-scattering moldings.
11. For the production of precision injection-molded parts, such as, for example, lens holders. To that end, polycarbonates having a content of glass fibers are used, which optionally contain, in addition, approximately from 1 to 10 wt. % $MoS_2$, based on the total weight.
12. For the production of parts for optical devices, especially lenses for photographic and film cameras (see, for example, DE-OS 2 701 173).
13. As light transmission carriers, especially as fiber-optic cables (see, for example, EP-A1 0 089 801).
14. As electrical insulating materials for electrical conductors and for plug housings as well as plug connectors.
15. Production of mobile phone casings having improved resistance to perfume, aftershave and perspiration.
16. Network interface devices.
17. As carrier material for organic photoconductors.
18. For the production of lamps, for example in the form of headlamps, headlight lenses or internal lenses.
19. For medical applications, for example, oxygenators, dialyzers.
20. For foodstuffs applications, such as, for example, bottles, kitchenware and chocolate molds.
21. For applications in the automotive sector, where contact with fuels and lubricants may occur, such as, for example, bumpers, optionally in the form of suitable blends with ABS or suitable rubbers.
22. For sports articles, such as, for example, slalom poles or ski boot buckles.
23. For domestic articles, such as, for example, kitchen sinks and letter box casings.
24. For casings, such as, for example, electrical distribution cabinets.
25. Casings for electric toothbrushes and hairdryer casings.
26. Transparent washing machines—bull's-eyes having improved resistance to the washing solution.
27. Safety goggles, optical corrective spectacles.
28. Lamp covers for kitchen appliances having improved resistance to cooking steam, especially oil vapors.
29. Packaging films for medicaments.
30. Chip boxes and chip carriers.
31. For other applications, such as, for example, stable doors or animal cages.

Polyester polycarbonates according to the invention containing structural units A and B in which the structural unit B is derived from the compounds of formulae IIa and IIb, but especially from formula III, and containing from 0.5 to 49 mol %, preferably from 2 to 40 mol %, particularly preferably from 10 to 25 mol %, based on 100 mol % of the bifunctional structural units A and B, of bifunctional ester structural units A, are especially suitable owing to their low rheooptical constant $C_R$ for the production of the data carriers according to the invention.

For the production of data carriers according to the invention in particular, the substrates must have a high degree of purity. That is achieved by reducing the content of residual monomers, solvents, foreign particles (of inorganic or organic nature, especially salts and dust) and of chlorine to the lowest possible values during working up and isolation of the substrate resin. That is described, for example, in EP-A 380 002 (pages 4 to 6) or EP-A 691 361 (pages 10 to 14), to the disclosure of which reference is therefore made.

The data carriers according to the invention may take various forms. Particular preference is given to known forms such as optical cards or cylindrical perforated disks such as in the case of compact disks (CD), CD recordables (CD-R), CD rewritables (CD-RW), digital versatile disks (DVD) or minidisks (MD).

Information storage layers (e.g., phase-change layers, magnetooptical layers, colorants, fluorescent colorants, photopolymers), dielectric (e.g., Si/N), reflective (e.g., silver, gold or aluminium), semi-reflective (e.g., Si, Ge), protective layers (e.g., acrylic lacquers) and further functional layers may be applied to the substrate. Various sequences of such layers are possible.

Several layers of the substrate or layers with other substrates may be laminated over one another. The stored information may be impressed into the surface (e.g., as a pit structure) or may be deposited in separate information layers. The information may be read through the transparent substrate or from the information side.

The invention relates also to optical information storage media in which the substrate material according to the invention is used in the form of films, for example, for covering the information layer in DVR (direct video recording), or as the substrate of multi-layer systems (optionally with impressed information).

The Examples which follow are intended to illustrate the invention, but without limiting it.

EXAMPLES

Example 1

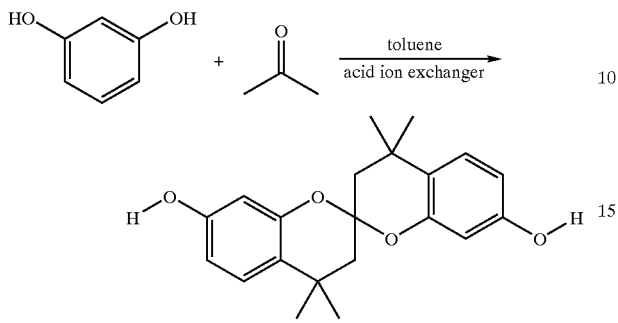

30 g (0.27 mol) of resorcinol and 23.5 g (0.405 mol) of acetone were dissolved in 300 ml of dry toluene. 50 g of anhydrous ion exchanger SC 104 (Bayer AG) were added as catalyst. Condensation to the product was carried out by boiling at reflux for 5.5 hours. When the reaction was completed, the ion exchanger was separated off and then washed with toluene. The toluene fractions were combined and concentrated to dryness. Drying in vacuo at 50° C. yielded 33.3 g of crude product, which was purified further by column chromatography.

There was obtained a white solid having the following analytical data:

Melting point: 200° C.

GC-MS: as TMS mass 484 (M=340)

HPLC-MS: M=340

$^1$H-NMR (400 MHz, $D_6$-DMSO, room temperature, TMS): δ=1.21–1.47 (d, 12H; $CH_3$); 1.92–2.06 (dd, 4H; —$CH_2$—); 5.96 (s, 2H; Ar—H); 6.35–6.37 (d, 2H; Ar—H); 7.12–7.17 (d, 2H; Ar—H); 9.02 (s, 2H; Ar—OH)

Preparation of polyester polycarbonates from the diphenol of Example 1 and dimer fatty acid Pripol 1009.

A. 10 wt. % Pripol 1009

The hydrogenated fatty acid used (Pripol 1009 from Uniqema) has the following specifications: iodine number <10, monomer content <0.1%, trimer content <1%. 0.42 g of phosgene was introduced at room temperature into a mixture of 1.22 g of Pripol 1009, 0.169 g of NaOH, 87.6 g of water and 175.1 ml of methylene chloride. The mixture was stirred briefly. A mixture of 10.21 g of diphenol of Example 1, 0.09 g of tert-butylphenol, 2.64 g of NaOH, 87.6 g of water and 0.04 ml of N-ethylpiperidine from a receiver vessel was then added. For the purposes of condensation, 5.93 g of phosgene were introduced, the pH value being maintained in the range from 12.5 to 12.8 by the occasional addition of sodium hydroxide solution.

After 30 minutes stirring, the batch was acidified with dilute phosphoric acid and then washed free of electrolytes with distilled water. The organic phase was separated off and concentrated in a rotary evaporator. The product was precipitated by introduction into methanol, isolated by filtration and dried under a water-jet vacuum.

Yield: 10.14 g of white polymer

Glass transition temperature (DSC, 2. heating): 160.8° C.

Molecular weight (BPA-PC calibration): Mw 10,340 g/mol

B. 13 wt. % Pripol 1009

A polyester polycarbonate was prepared in an analogous manner from the diphenol of Example 1 and Pripol 1009 using 13 wt. % Pripol 1009. For isolation of the polymer, the organic phase was concentrated to dryness (no precipitation).

Molecular weight (BPA-PC calibration): Mw 43,860 g/mol
Glass transition temperature (DSC, 2. heating): 137.8° C.
Water content: 0.32%
  0.31% (1st repetition)
  0.32% (2nd repetition)
  0.29% (3rd repetition)

Examples of substituted spirochromans according to the invention:

Example 2

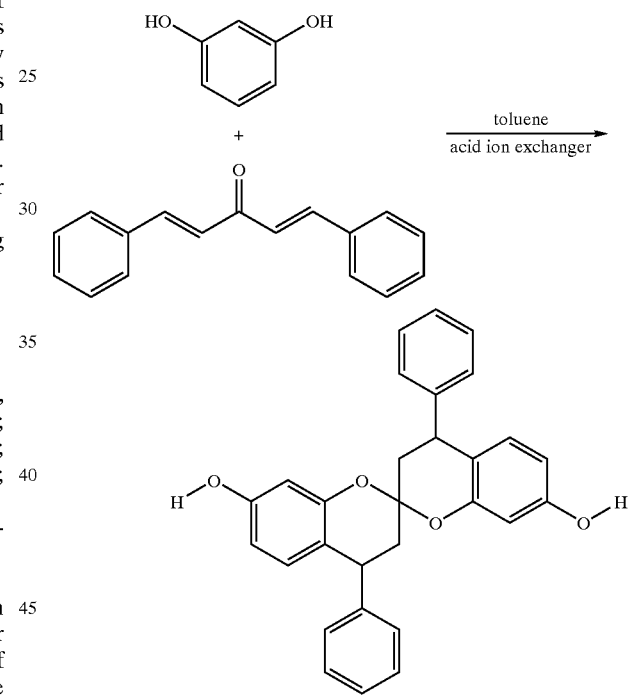

10 g (0.09 mol) of resorcinol and 10.64 g (0.045 mol) of trans,trans-1,5-diphenyl-1,4-pentadien-3-one (Aldrich) were dissolved in 150 ml of dry toluene. 25 g of anhydrous ion exchanger SC 104 (Bayer AG) were added as catalyst. Condensation to the product was carried out by boiling at reflux for 6 hours. When the reaction was completed, the ion exchanger was separated off and then washed with toluene. The toluene fractions were combined and concentrated to dryness. Drying in vacuo at 50° C. yields 17.4 g of crude product, which was purified further by column chromatography. There was obtained a yellowish solid having the following analytical data:

GC-MS: as TMS mass 580 (M=436, cis, trans)

Example 3

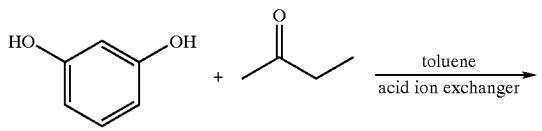

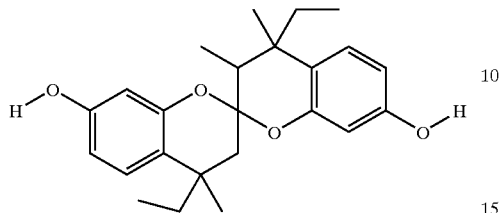

30 g (0.27 mol) of resorcinol and 29.2 g (0.405 mol) of methyl ethyl ketone (MEK) were dissolved in 300 ml of dry toluene. 50 g of anhydrous ion exchanger K1221 (Bayer AG) were added as catalyst. Condensation to the product was carried out by boiling at reflux for 6 hours. When the reaction was completed, the ion exchanger was separated off and then washed with toluene. The toluene fractions were combined and concentrated to dryness. Drying in vacuo at 50° C. yields 50.4 g of crude product, which was purified further by column chromatography. There was obtained a white solid having the following analytical data:

GC-MS: as TMS mass 526 (M=382, stereoisomers)
HPLC-MS: M=382

Example 4

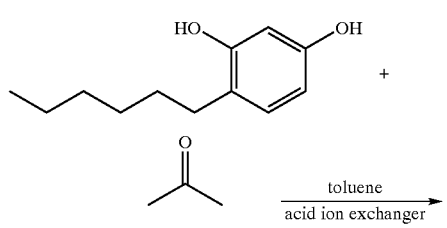

-continued

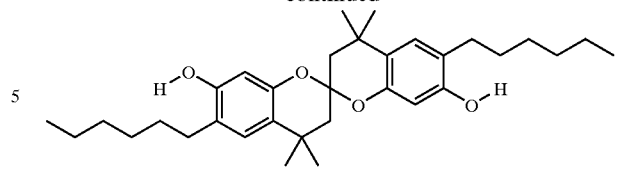

52.45 g (0.27 mol) of 4-hexylresorcinol and 23.5 g (0.405 mol) of acetone were dissolved in 300 ml of dry toluene. 50 g of anhydrous ion exchanger K1221 (Bayer AG) were added as catalyst. Condensation to the product was carried out by boiling at reflux for 6 hours. When the reaction was complete, the ion exchanger was separated off and then washed with toluene. The toluene fractions were combined and concentrated to dryness. Drying in vacuo at 50° C. yielded 61.6 g of crude product, which was purified further by column chromatography.

There was obtained a white solid having the following analytical data:

GC-MS: as TMS mass 652 (M=508)

Example 5

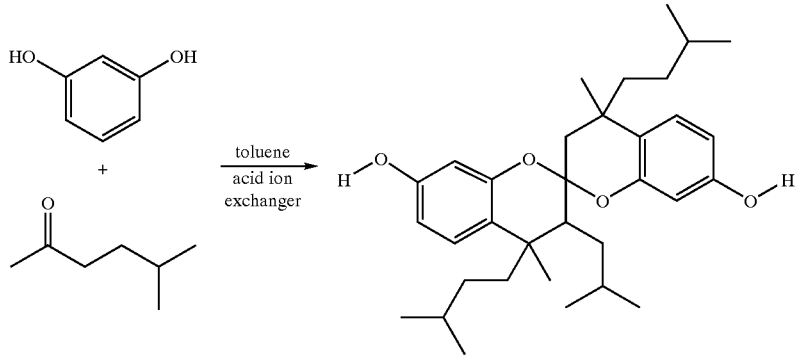

30 g (0.27 mol) of resorcinol and 46.25 g (0.405 mol) of 5-methyl-2-hexanone were dissolved in 300 ml of dry toluene. 50 g of anhydrous ion exchanger K1221 (Bayer AG) were added as catalyst. Condensation to the product was carried out by boiling at reflux for 6 hours. When the reaction was completed, the ion exchanger was separated off and then washed with toluene. The toluene fractions were combined and concentrated to dryness. Drying in vacuo at 50° C. yields 63.4 g of crude product (still contains toluene), which was purified further by column chromatography.

There is obtained a yellowish-white solid having the following analytical data:

HPLC-MS: M=508

Example 6

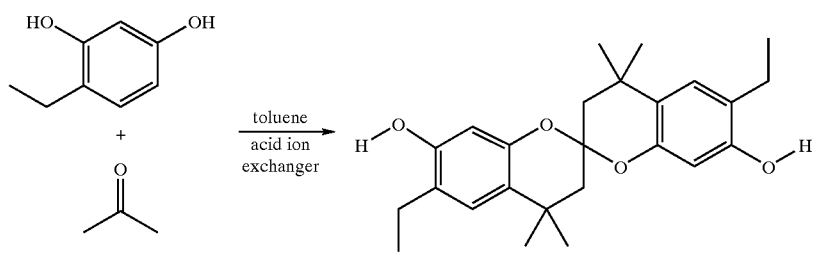

37.31 g (0.27 mol) of 4-ethylresorcinol and 23.5 g (0.405 mol) of acetone were dissolved in 300 ml of dry toluene. 50 g of anhydrous ion exchanger SC 104 (Bayer AG) were added as catalyst. Condensation to the product was carried out by boiling at reflux for 2 days. When the reaction was complete, the ion exchanger was separated off and then washed with toluene. The resulting precipitate was dried in vacuo at 50° C., yielding 3.35 g of product, which did not require further purification by column chromatography.

There was obtained a light-beige solid having the following analytical data:

GC-MS: as TMS mass 540 (M=396)
HPLC-MS: M=396
$^1$H-NMR (400 MHz, $D_6$-DMSO, room temperature, TMS): δ=1.07–1.11 (t, 6H; $CH_2$–$CH_3$); 1.22–1.46 (d, 12H; $CH_3$); 1.85–2.03 (dd, 4H; —$CH_2$—); 2.42–2.5 (q, 4H, —$CH_2$–$CH_3$); 6.0 (s, 2H; Ar—H); 7.0 (s, 2H; Ar—H); 8.86 (s, 2H; Ar—OH)

Example 7

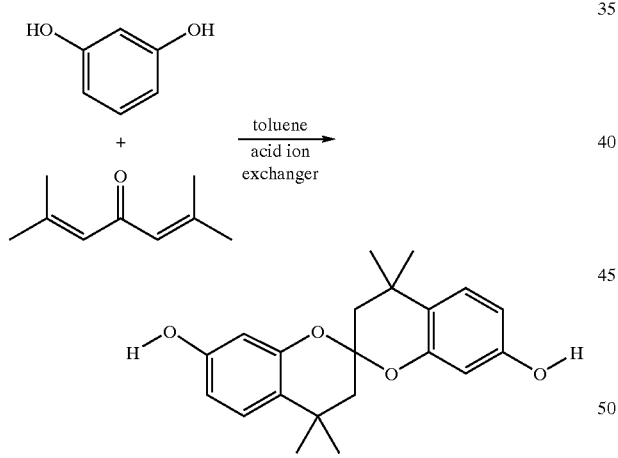

30 g (0.27 mol) of resorcinol and 18.66 g (0.135 mol) of phorone (Aldrich) were dissolved in 300 ml of dry toluene. 50 g of anhydrous ion exchanger SC 104 (Bayer AG) were added as catalyst. Condensation to the product was carried out by boiling at reflux for 8 hours, with water separation. When the reaction was completed, the ion exchanger was separated off and then washed with toluene. The resulting precipitate was dried in vacuo at 50° C., yielding 40.1 g of crude product (still contains toluene), which was purified further by column chromatography.

There was obtained a white solid having the following analytical data:

GC-MS: as TMS mass 484 (M=340)
HPLC-MS: M=340

NMR characterisation see also Example 1

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Polyestercarbonate resin the molecular structure of which comprise units derived from dicarboxylic acids of formula (I)

wherein T represents a branched or linear, saturated or unsaturated alkyl, arylalkyl or cycloalkyl moiety of from 8 to 40 carbons, and units derived from at least one diphenol selected from the group consisting of formula (IIa) and (IIb)

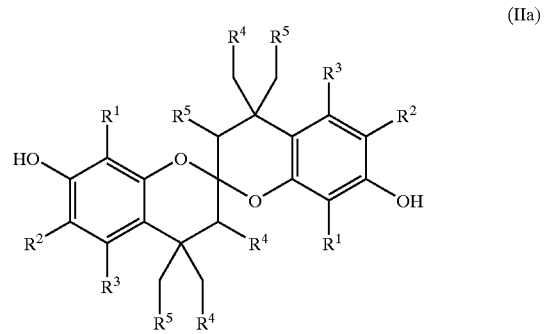

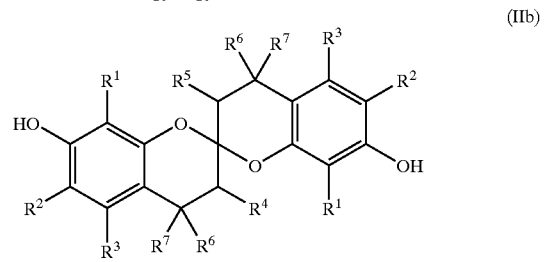

in which $R_1$ to $R_7$ each independently of the others represents hydrogen, halogen, a $C_1$- to $C_{12}$-alkyl radical, a $C_6$- to $C_{19}$-aryl radical, a $C_7$- to $C_{12}$-aralkyl radical.

2. The polyestercarbonate according to claim 1 wherein structural units of both diphenols conforming to IIa and IIb are present.

3. Diphenols of formula (IIa) and/or (IIb)

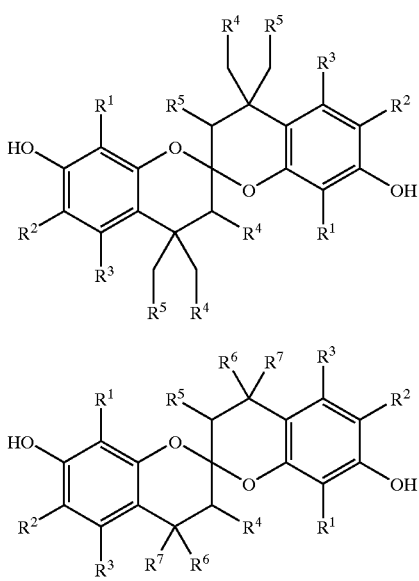

in which $R_1$ to $R_7$ each independently of the others represents hydrogen, halogen, a $C_1$- to $C_{12}$-alkyl radical, a $C_6$- to $C_{19}$-aryl radical, a $C_7$- to $C_{12}$-aralkyl radical, with the exception of compounds in which $R^1$ to $R^5$ in formula IIa are hydrogen and $R^6$ and $R^7$ in formula IIb are simultaneously methyl groups.

4. The polyesterpolycarbonate according to claim 1, having weight average molecular weight $M_w$ of 7000 to 40,000.

5. A molded article comprising the polyesterpolycarbonate according to claim 1.

6. Machine-readable data carrier wherein substrate comprise the polyester polycarbonate according to claim 1.

7. A process for the preparation of the polyesterpolycarbonates according to claim 1, comprising reacting at least one diphenol of formula IIa and/or IIb and at least one dicarboxylic acid of formula I with at least one carbonic acid derivative.

8. A method of using the diphenols of claim 3 comprising producing a polyesterpolycarbonate.

9. A Process for the preparation of the diphenols of claim 3 by comprising acid condensing ketones or phorones with substituted or unsubstituted resorcinols.

10. A method of using the diphenols of claim 3 comprising producing a polycarbonate.

11. A thermoplastic molding composition comprising the polyestercarbonate of claim 1.

* * * * *